United States Patent
Kiener et al.

[11] Patent Number: 5,994,540
[45] Date of Patent: Nov. 30, 1999

[54] DI-AND TRISUBSTITUTED PYRIDINES AND THEIR PREPARATION

[75] Inventors: Andreas Kiener, Visp; Jean-Paul Roduit, Grone; Alain Wellig, Ried-Mörel, all of Switzerland

[73] Assignee: Lonza, Ltd., Gampel/Valais, Switzerland

[21] Appl. No.: 09/069,996

[22] Filed: Apr. 30, 1998

Related U.S. Application Data

[62] Division of application No. 08/561,230, Nov. 21, 1995, Pat. No. 5,760,236.

[30] Foreign Application Priority Data

Nov. 25, 1994 [CH] Switzerland ............................. 3537/94
Nov. 25, 1994 [CH] Switzerland ............................. 3538/94

[51] Int. Cl.[6] ...................... C07D 401/04; C07D 403/04; C12Q 1/02
[52] U.S. Cl. ...................... 544/238; 546/291; 546/284.4; 546/301; 435/29
[58] Field of Search .............................................. 544/238

[56] References Cited

U.S. PATENT DOCUMENTS 5,760,236  6/1998  Kiener et al. ........................... 546/291

OTHER PUBLICATIONS

Chemical Abstracts, vol. 91, (5), abst.no.39511w (Jul. 30, 1979).

*Primary Examiner*—Alan L. Rotman
*Attorney, Agent, or Firm*—Fisher, Christen & Sabol

[57] ABSTRACT

Substituted pyridines of the general formula:

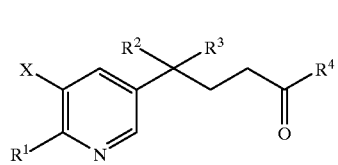

I wherein $R^1$ is hydroxyl or chlorine, and a) X is hydrogen or chlorine, $R^2$ and $R^3$ together are =O, $R^4$ is a group of the formula —$OR^5$ and $R^5$ is hydrogen, $C_1$–$C_4$-alkyl or benzyl or b) X is hydrogen and $R^2$, $R^3$ and $R^4$ together are =N—NH—, or c) X and $R^2$ each is hydrogen and $R^3$ and $R^4$ together are —O—, or d) X and $R^2$ each is hydrogen, $R^3$ is hydroxyl and $R^4$ is amino or hydroxy.

The compounds are obtained by subjecting nicotine to microbiological oxidation to give 5-succinoyl-2-pyridone, followed by chemical reactions. The compounds are suitable as intermediates for the preparation of pharmaceutically active compounds.

1 Claim, No Drawings

DI-AND TRISUBSTITUTED PYRIDINES AND THEIR PREPARATION

CROSS-REFERENCE

This application is a divisional of Ser. No. 08/561,230 filed Nov. 21, 1995, U.S. Pat. No. 5,760,236.

BACKGROUND OF THE INVENTION

1. Field of the Invention

The invention relates to novel 2,5-di- and 2,3,5-trisubstituted pyridines and to processes for their preparation from nicotine.

2. Background Art 2,5-disubstituted (or, in the case of alternative numbering, 3,6-disubstituted) pyridines such as, 6-hydroxynicotinic or 6-chloronicotinic acid, are valuable chemical intermediates, for example, for the preparation of retinoid analogues (U.S. Pat. No. 5,089,509) or renin inhibitors (U.S. Pat. No. 5,098,924).

The 2,5-disubstituted pyridines which could be obtained to date on an industrial scale are compounds which, like 6-hydroxynicotinic acid, as a rule have attached one $C_1$ radical only in the 5- (or 3-) position.

To prepare compounds having longer carbon chains, this $C_1$ radical must be extended by means of conventional synthetic methods with C-C coupling (U.S. Pat. No. 5,089,509, column 13). Since this method is complicated and expensive, it was desirable to obtain compounds having longer side chains and functional groups which can be used for further synthetic steps in a simpler fashion. It was, furthermore, desirable to make accessible compounds of this class which have attached to them a chlorine atom as an additional substituent in the 3-position of the pyridine ring (if numbered as 2-pyridone).

BROAD DESCRIPTION OF THE INVENTION

An object of the invention is to provide novel 2,5-disubstituted pyridines having longer side chains in the 5-position and, if appropriate, a chlorine atom in the 3-position of the pyridine ring, and to provide a simple route or process to obtain these novel compounds starting from readily accessible educts. Other objects and advantages of the invention are set out herein or are obvious herefrom to one skilled in the art.

The objects and advantages of the invention are achieved by the compounds and processes of the invention.

The invention involves substituted pyridines of the general formula:

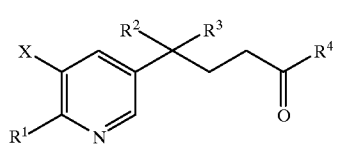

I wherein $R^1$ is hydroxyl or chlorine and
a) X is hydrogen or chlorine, $R^2$ and $R^3$ together are =O, $R^4$ is a group of the formula —$OR^5$ and $R^5$ is hydrogen, $C_1$–$C_4$-alkyl or benzyl, or
b) X is hydrogen and $R^2$, $R^3$ and $R^4$ together are =N—NH—, or
c) X and $R^2$ each is hydrogen and $R^3$ and $R^4$ together —O—, or
d) X and $R^2$ each is hydrogen, $R^3$ is hydroxyl and $R^4$ is amino or hydroxyl, with the exception of the substituted pyridine of formula I, where X is H, $R^1$ and $R^4$ each is —OH and $R^2$ and $R^3$ together are =O.

The invention also involves the process for the preparation of the invention 2,5-disubstituted pyridines of formula L wherein X is hydrogen and $R^2$, $R^3$ and $R^4$ together form a =NH—NH— group. In a first step, nicotine is oxidized to give 5-succinoyl-2-pyridone using a microorganism of the genus Pseudomonas or Variovorax. The 5-succinoyl-2-pyridone is esterified with a $C_1$–$C_4$-alkanol or benzyl alcohol to give the corresponding $C_1$–$C_4$-alkyl or benzyl ester of the formula:

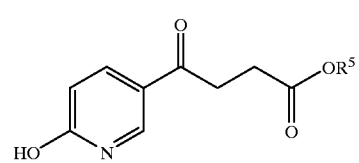

II wherein $R^5$ is $C_1$–$C_4$-alkyl or benzyl. If appropriate, the ester of formula II is converted into the corresponding chlorine compound by exchanging the hydroxyl group for chlorine. The ester or corresponding chlorine compound is cyclized with hydrazine to give the pyridazinone derivative of the formula:

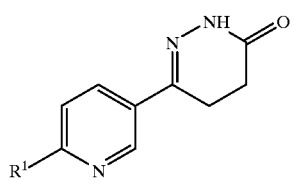

III

Preferably a microorganism from the group consisting of Pseudomonas putida DSM 8231, Pseudomonas putida DSM 8236, Pseudomonas fluorescens DSM 8235, Pseudomonas sp. DSM 8653, or Variovorax paradoxus (=Alcaligenes paradoxus) DSM 8244, is employed for the microbiological oxidation. Preferably, the $C_1$–$C_4$ alkyl or benzyl ester (II) is converted into the chloro compound by hydroxyl group exchange using phosphorus oxychloride.

The invention involves the process for the preparation of 2,5-disubstituted pyridines of formula I wherein X is hydrogen, $R^1$ is chlorine, $R^2$ is hydrogen and $R^3$ and $R^4$ together are —O—. In a first step, nicotine is oxidized to give 5-succinoyl-2-pyridone using a microorganism of the genus Pseudomonas or Variovorax. The 5-succinoyl-2-pyridone is esterified with a $C_1$–$C_4$-alkanol or benzyl alcohol to give the corresponding $C_1$–$C_4$-alkyl or benzyl ester of the formula:

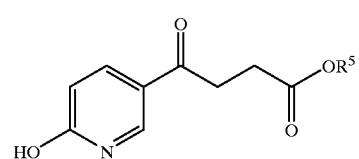

II wherein $R^5$ is $C_1$–$C_4$-alkyl or benzyl. The ester of formula II is converted into the corresponding chlorine compound by exchanging the hydroxyl group for chlorine. The corresponding chlorine compound is reduced and cyclized to give the lactone of the formula:

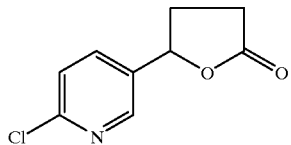

IV

Preferably a microorganism from the group consisting of *Pseudomonas putida* DSM 8231, *Pseudomonas putida* DSM 8236, *Pseudomonas fluorescens* DSM 8235, Pseudomonas sp. DSM 8653, or *Variovorax paradoxus* (=*Alcaligenes paradoxus*) DSM 8244, is employed for the microbiological oxidation. Preferably the $C_1$–$C_4$ alkyl or benzyl ester (II) is converted into the chloro compound by hydroxyl group exchange using phosphorus oxychloride. Preferably the ester (II) is reduced to the lactone (IV) using sodium borohydride as the reducing agent.

The invention also involves a process for the preparation of 2,5-disubstituted pyridines of formula I wherein X is hydrogen, $R^1$ is chlorine, $R^2$ is hydrogen, $R^3$ is hydroxyl and $R^4$ is amino or hydroxyl. In a first step, nicotine is oxidized to give 5-succinoyl-2-pyridone using a microorganism of the genus Pseudomonas or Variovorax. The 5-succinoyl-2-pyridone is esterified with a $C_1$–$C_4$-alkanol or benzyl alcohol to give the corresponding $C_1$–$C_4$-alkyl or benzyl ester of the formula:

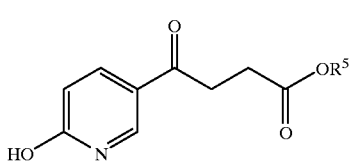

II wherein $R^5$ is $C_1$–$C_4$-alkyl or benzyl. The ester of formula II is converted into the corresponding chlorine compound by exchanging the hydroxyl group for chlorine. The corresponding chlorine compound is reduced and cyclized to give the lactone of the formula:

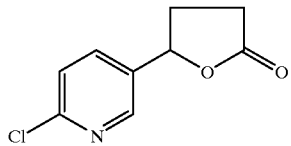

IV

Finally, the lactone is converted with ammonia or an aqueous strong base into the amide or the acid of the formula:

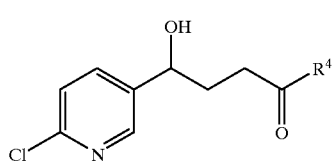

V wherein $R^4$ has the above-mentioned meaning. Preferably a microorganism from the group consisting of *Pseudomonas putida* DSM 8231, *Pseudomonas putida* DSM 8236, *Pseudomonas fluorescens* DSM 8235, Pseudomonas sp. DSM 8653, or *Variovorax paradoxus* (=*Alcaligenes paradoxus*) DSM 8244, is employed for the microbiological oxidation Preferably the $C_1$–$C_4$ alkyl or benzyl ester (II) is converted into the chloro compound by hydroxyl group exchange using phosphorus oxychloride. Preferably the ester (II) is reduced to the lactone (IV) using sodium borohydride as the reducing agent.

The invention involves a process for the preparation of a 2,3,5-trisubstituted pyridine of formula I wherein X is chlorine, $R^1$ is hydroxyl, $R^2$ and $R^3$ together are =O and $R^4$ is hydroxyl. In a first step, nicotine is oxidized to give 5-succinoyl-2-pyridone using a microorganism of the genus Pseudomonas or Variovorax. The 5-succinoyl-2-pyridone is chlorinated in a second step to 3-chloro-5-succinoyl-2-pyridone using chlorine in alkaline solution.

The invention also involves a process for the preparation of 2,3,5-trisubstituted pyridines of formula I wherein X is chlorine, $R^1$ is hydroxyl, $R^2$ and $R^3$ together are =O, $R^4$ is $OR^5$ and $R^5$ is $C_1$–$C_4$-alkyl or benzyl. In a first step, nicotine is oxidized to give 5-succinoyl-2-pyridone using a microorganism of the genus Pseudomonas or Variovorax. The 5-succinoyl-2-pyridone is chlorinated, in a second step, to give 3-chloro-5-succinoyl-2-pyridone (formula I, X is Cl, $R^1$ is OH, $R^2$ and $R^3$ together are =O, and $R^4$ is OH) using chlorine in an alkaline solution. The pyridone is finally esterified, in a third step, with a $C_1$–$C_4$-alkanol or benzyl alcohol to give the $C_1$–$C_4$-alkyl or benzyl ester.

The invention further involves a process for the preparation of 2,3,5-trisubstituted pyridines of formula I wherein X is chlorine, $R^1$ is chlorine, $R^2$ and $R^3$ together are =O, $R^4$ is $OR^5$ and $R^5$ is $C_1$–$C_4$-alkyl or benzyl. In a first step, nicotine is oxidized to give 5-succinoyl-2-pyridone using a microorganism of the genus Pseudomonas or Variovorax. The 5-succinoyl-2-pyridone is chlorinated, in a second step, to give 3-chloro-5-succinoyl-2-pyridone (formula I, X is Cl, $R^1$ is OH, $R^2$ and $R^3$ together are =O, and $R^4$ is OH) using chlorine in an alkaline solution. The pyridone is esterified, in a third step, with a $C_1$–$C_4$-alkanol or benzyl alcohol to give the $C_1$–$C_4$-alkyl or benzyl ester. The ester is converted into the 2,3-dichloro compound by exchanging the hydroxyl group for chlorine. Preferably, phosphorus oxychloride is employed as the reagent for exchanging the hydroxyl group for chlorine. Preferably, a microorganism from the group consisting of *Pseudomonas putida* DSM 8231, *Pseudomonas putida* DSM 8236, *Pseudomonas fluorescens* DSM 8235, Pseudomonas sp. DSM 8653, *and Variovorax paradoxus* (=*Alcaligenes paradoxus*) DSM 8244, is employed for the nicotine oxidation.

DETAILED DESCRIPTION OF THE INVENTION

It has been found that the renewable resource nicotine, of which large amounts are available, can be used for obtaining 5-succinoyl-2-pyridone(4-(1,6-dihydro-6-oxopyridin-3-yl)-4-oxobutyric acid), which is known, on an industrially usable scale by means of microbiological oxidation using microorganisms of the genera Pseudomonas and Variovorax and chemically converting this compound into novel 2,5-disubstituted pyridines having a $C_4$-side chain or a suitable heterocyclic radical in the 5-position of the pyridine ring. As is known, the 2-pyridones mentioned here and in the following text are compounds which are capable of tautomerism and can also exist in the 2-hydroxypyridine form or in the form of a mixture of the two tautomeric forms. If, in the following text, in each case only one of the two forms which are possible is mentioned or shown as a structural formula, this is always to be understood as meaning both forms, independently of the form in which the compound in question actually exists.

The fact that nicotine can be oxidized microbiologically to give 5-succinoyl-2-pyridone is known, for example, from German OS 2,634,188.

However, it has been found that particularly high yields and product concentrations can be obtained when using certain strains of Pseudomonas or Variovorax, in particular when relatively high nicotine concentrations are maintained.

The microorganisms which are preferably used were isolated from sewage sludge or soil by means of customary microbiological techniques and selected using nicotine as the growth substrate. They were deposited at the DSM—Deutsche Sammlung von Mikroorganismen und Zellkulturen [German Collection of Microorganisms and Cell Cultures] GmbH, Mascheroder Weg 1b, D-38124 Braunschweig. The details concerning isolation and selection are described in Example 1.

The scientific (taxonomic) description and properties of strains *P. putida* DSM 8231, *P. fluorescens* DSM 8235, *P. putida* DSM 8236, Pseudomonas sp. DSM 8653 and *V. paradoxus* DSM 8244 are compiled in the following tables.

TABLE 1

Identification of strain DSM 8231 (DSM ID 93-202)

*Pseudomonas putida*

Strain Characteristics

| | | | |
|---|---|---|---|
| Cell shape | Rods | NO$_2$ from NO$_3$ | − |
| Width in μm | 0.8–1.0 | Denitrification | − |
| Length in μm | 1.5–2.5 | Phenylalanine deaminase | − |
| Motility | + | Levan from sucrose | − |
| Gram reaction | − | Lecithinase | − |
| Lysis by 3% KOH | + | Urease | − |
| Aminopeptidase (Cerny) | + | Hydrolysis of | |
| Spores | − | starch | − |
| Oxidase | + | gelatine | − |
| Catalase | + | casein | − |
| Growth | | DNA | − |
| anaerobic | − | Tween 80 | − |
| 37°/41° C. | +/− | aesculin | − |
| pH 5.7 | + | Tytosine metabolization | + |
| MacConkey agar | + | Substrate utilization | |
| SS agar | + | acetate | + |
| cetrimide agar | + | adipate | − |
| Pigments | | caprate | + |
| fluorescent | + | citrate | + |
| pyocyanin | − | glycolate | + |
| Acid from (OF test) | | levulinate | − |
| glucose aerobic | + | malate | + |
| glucose anaerobic | − | malonate | + |
| glucose aerobic with alkaline reaction | − | phenylacetate | + |
| | | L-arabinase | + |
| Gas from glucose | − | D-fructose | + |
| Acid from (ASS) | | D-glucose | + |
| D-glucose | + | D-mannose | + |
| D-fructose | + | maltose | − |
| D-xylose | + | D-xylose | + |
| ONPG/PNPG | − | mannitol | − |
| ADH | + | gluconate | + |
| VP | − | 2-ketogluconate | + |
| Indole | − | N-acetylglucosamine | − |
| | | L-serine | + |

TABLE 1-continued

Identification of strain DSM 8231 (DSM ID 93-202)

*Pseudomonas putida*

Result:

Strain DSM 8231 = *Pseudomonas putida*

TABLE 2

Identification of strain DSM 8236 (DSM ID 93-229)

*Pseudomonas putida*

Strain Characteristics

| | | | |
|---|---|---|---|
| Cell shape | Rods | NO$_2$ from NO$_3$ | − |
| Width in μm | 0.8–0.9 | Denitrification | − |
| Length in μm | 1.5–4.5 | Phenylalanine deaminase | − |
| Motility | + | Levan from sucrose | − |
| Gram reaction | − | Lecithinase | − |
| Lysis by 3% KOH | + | Urease | − |
| Aminopeptidase (Cerny) | + | Hydrolysis of | |
| Spores | − | starch | − |
| Oxidase | + | gelatine | − |
| Catalase | + | casein | − |
| Growth | | DNA | − |
| anaerobic | − | Tween 80 | − |
| 37°/41° C. | +/− | aesculin | − |
| pH 5.7 | + | Tyrosine metabolization | + |
| MacConkey agar | + | Substrate utilization | |
| SS agar | + | acetate | + |
| cetrimide agar | + | adipate | − |
| Pigments | | caprate | + |
| fluorescent | + | citrate | + |
| pyocyanin | − | glycolate | + |
| Acid from (OF test) | | levulinate | + |
| glucose aerobic | + | malate | + |
| glucose anaerobic | − | malonate | − |
| glucose aerobic with alkaline reaction | − | phenylacetate | + |
| | | L-arabinose | − |
| Gas from glucose | − | D-fructose | + |
| Acid from (ASS) | | D-glucose | + |
| D-glucose | + | D-mannose | + |
| D-fructose | + | maltose | − |
| D-xylose | + | D-xylose | + |
| ONPG/PNPG | − | mannitol | − |
| ADH | + | gluconate | + |
| VP | − | 2-ketogluconate | − |
| Indole | − | N-acetylglucosamine | − |
| | | L-serine | + |

Result:

Strain DSM 8236 = *Pseudomonas putida*

TABLE 3

Identification of strain DSM 8235 (DSM ID 93-207)

*Pseudomonas fluorescens*

Strain Characteristics

| | | | |
|---|---|---|---|
| Cell shape | Rods | NO$_2$ from NO$_3$ | + |
| Width in μm | 1.0 | Denitrification | − |
| Length in μm | 2.0–3.0 | Phenylalanine deaminase | − |

TABLE 3-continued

Identification of strain DSM 8235 (DSM ID 93-207)

*Pseudomonas fluorescens*

| | | | |
|---|---|---|---|
| Motility | + (up to 24!) | Levan from sucrose | − |
| Gram reaction | − | Lecithinase | − |
| Lysis by 3% KOH | + | Urease | − |
| | | Hydrolysis of | |
| Aminopeptidase (Cerny) | + | starch | − |
| Spores | − | gelatine | − |
| Oxidase | + | casein | − |
| Catalase | + | DNA | − |
| Growth | | Tween 80 | − |
| anaerobic | − | aesculin | − |
| 37°/41° C. | −/− | Tyrosine metabolization | + |
| pH 5.7 | + | Substrate utilization | |
| MacConkey agar | + | acetate | + |
| SS agar | + | adipate | − |
| cetrimide agar | + | caprate | + |
| Pigments | | citrate | + |
| fluorescent | − | glycolate | − |
| pyocyanin | − | levulinate | + |
| Acid from (OF test) | | malate | + |
| glucose, aerobic | + | malonate | + |
| glucose anaerobic | − | phenylacetate | + |
| glucose aerobic with alkaline reaction | − | L-arabinose | + |
| | | D-fructose | + |
| Gas from glucose | − | D-glucose | + |
| Acid from (ASS) | | D-mannose | + |
| D-glucose | + | maltose | − |
| D-fructose | + | D-xylose | + |
| D-xylose | + | mannitol | + |
| ONPG/PNPG | − | gluconate | + |
| ADH | + | 2-ketogluconate | + |
| VP | − | N-acetylglucosamine | − |
| Indole | − | L-serine | + |
| | | Result | |
| | | Strain DSM 8235 = *Pseudomonas fluorescens* | |

TABLE 4

Identification of strain DSM 8244 (DSM ID 93-204)

*Variovorax paradoxus*
(= *Alcaligenes paradoxus*)

Strain Characteristics

| | | | |
|---|---|---|---|
| Cell shape | Rods | NO₂ from NO₃ | − |
| Width in μm | 0.8–1.0 | Denitrification | − |
| Length in μm | 1.5–3.5 | Phyenylalanine deaminase | − |
| Motility | + | Levan from sucrose | − |
| Gram reaction | − | Lecinthinase | − |
| Lysis by 3% KOH | + | Urease | − |
| Aminopeptidase (Cerny) | + | Hydrolysis of | |
| Spores | − | starch | − |
| Oxidase | + | gelatine | − |
| Catalase | + | casein | − |
| Growth | | DNA | − |
| anaerobic | − | Tween 80 | + |
| 37°/41° C. | −/− | aesculin | − |
| pH 5.7 | − | Tyrosine metabolization | + |
| MacConkey agar | + | Substrate utilization | |
| SS agar | − | acetate | + |
| cetrimide agar | − | adipate | + |

TABLE 4-continued

Identification of strain DSM 8244 (DSM ID 93-204)

*Variovorax paradoxus*
(= *Alcaligenes paradoxus*)

| | | | |
|---|---|---|---|
| Pigments | | caprate | + |
| non-diffusible | − | citrate | + |
| diffusible | − | glycolate | + |
| fluorescent | − | levulinate | + |
| pyocyanin | − | malate | + |
| Acid from (OF test) | | malonate | − |
| glucose aerobic | w? | phenylacetate | + |
| glucose anaerobic | − | L-arabinose | + |
| glucose aerobic with alkaline reaction | − | D-fructose | + |
| | | D-glucose | + |
| Gas from glucose | − | D-mannose | + |
| Acid from (ASS) | | maltose | − |
| D-glucose | + | D-xylose | + |
| D-fructose | + | mannitol | + |
| D-xylose | + | gluconate | + |
| ONPG/PNPG | − | 2-ketogluconate | + |
| ADH | − | N-acetylglucosamine | + |
| VP | − | L-serine | − |
| Indole | − | Result: | |
| | | Strain DSM 8244 = *Variovorax paradoxus* (= *Alcaligenes paradoxus*) | |

TABLE 5

Scientific data (taxonomic data) for strain DSM 8653

*Pseudomonas putida*

| Strain characteristics | |
|---|---|
| Nitrate reduction | − |
| Indole production | − |
| Acid from glucose (anaerobic) | − |
| Arginine dihydrolase | + |
| Urease | − |
| β-Glucosidase | − |
| Protease | − |
| β-Galactosidase | − |
| Cytochrome oxidase | + |
| Assimilation of: | |
| Glucose | + |
| Arabinose | − |
| Mannose | − |
| Mannitol | − |
| N-Acetyl-glucosamine | − |
| Maltose | − |
| Guconate | + |
| Caprate | + |
| Adipate | − |
| Malate | + |
| Citrate | + |
| Phenylacetate | + |

The biotransformation of nicotine to 5-succinoyl-2-pyridone is carried out in the customary manner under aerobic conditions by growing an inoculum with which a fermenter is inoculated. Advantageously, part of the substrate (nicotine) is initially introduced and the remainder is fed in continuously. The nicotine concentration during the transformation is expediently 1 to 50 g/l preferably 5 to 20 g/l. The pH during the transformation is expediently in the range of 4 to 9, preferably at approximately 7. It is preferably kept constant by a controlled addition of acid and/or base. The temperature during the transformation is expediently between 20° and 50° C., preferably 25° to 45° C. The product can be isolated from the cell-free culture supernatant in the customary manner, for example, by precipitation with acid and filtration.

The biotransformation is preferably carried out with the strains P. putida DSM 8231, P. fluorescens DSM 8235, P. putida DSM 8236, V. paradoxus DSM 8244 or P. sp. DSM 8653, all of which have been mentioned already.

The compounds according to the invention are derived from 5-succinoyl-2-pyridone and are described by the general structural formula:

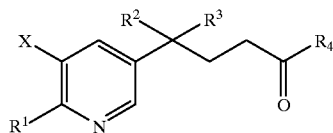

I where $R^1$ represents hydroxyl or chlorine. As mentioned already, the compounds where $R^1$ is hydroxyl may also exist in the 2-pyridone form.

General formula I encompasses the following groups of compounds:

(a) X is hydrogen or chlorine, $R^2$ and $R^3$ together are =O and $R^4$ is an —$OR^5$ group wherein $R^5$ is hydrogen, $C_1$–$C_4$-alkyl or benzyl. Compounds which correspond to this case are the 4-(pyridin-3-yl)-4-oxobutyric acids, which are substituted in the 2- (or 6-) position and, if appropriate, in the 3- (or 5-) position of the pyridine ring, and the $C_1$–$C_4$-alkyl and benzyl esters thereof, with the exception of the 5-succinoyl-2-pyridone where $R^1$ and $R^4$ each is —OH.

(b) X is hydrogen and $R^2$, $R^3$ and $R^4$ together form an =N—NH— group, so that this together with the $C_4$ side chain is a tetrahydropyridazine ring.

(c) X is hydrogen, $R^2$ is hydrogen and $R^3$ and $R^4$ together are —O—. Compounds which correspond to this case are the lactones of the 4-(pyridin-3-yl)-4hydroxybutyric acid which are substituted in the 2- (or 6-) position of the pyridine.

(d) X is hydrogen, $R^2$ is hydrogen, $R^3$ is hydroxyl and $R^4$ is amino or hydroxyl. Compounds which correspond to this case are the 4-(pyridin-3-yl)-4hydroxybutyric acids which are substituted in the 2- (or 6-) position of the pyridine ring and their amides.

The novel compounds of the first group where X is hydrogen can be obtained by esterifying 5-succinoyl-2-pyridone, which has been obtained from nicotine as described above, with $C_1$–$C_4$-alkanols or benzyl alcohol to give the corresponding $C_1$–$C_4$-alkyl or benzyl ester of the formula:

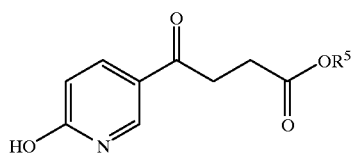

II wherein $R^5$ is $C_1$–$C_4$-alkyl or benzyl, and, if appropriate, exchanging the hydroxyl group for chlorine. If the hydroxyl group is exchanged for chlorine, phosphorus oxychloride is preferably employed as the reagent.

2-Chloro-5-succinoylpyridine ($R^1$ is Cl, $R^2$ and $R^3$ together are =O, $R^4$ is OH) can be prepared for example by hydrolyzing a corresponding alkyl ester or benzyl ester.

The compounds of the second group with a tetrahydropyridazine ring ($R^2$, $R^3$ and $R^4$ together are =N+NH—) are prepared according to the invention by first subjecting nicotine to microbiological oxidation as described above to give 5-succinoyl-2-pyridone, subsequently esterifying the product to give the alkyl ester (II), again as already described, then, if appropriate, converting this product into the corresponding chlorine compound by exchanging the hydroxyl group for chlorine, and finally cyclizing the product with hydrazine to give the pyridazinone derivative of the formula:

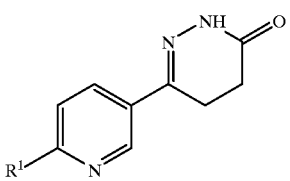

III

For the cyclization reaction, the hydrazine is advantageously employed in the form of the hydrazine hydrate. Of course, one can also use anhydrous hydrazine. The reaction with hydrazine (hydrate) is preferably carried out in a polar solvent, for example, in methanol or ethanol. The reaction temperature is expediently 0° to 100° C.

The lactone of 4-(6-chloropyridine-3-yl)-4-hydroxybutyric acid is prepared according to the invention by first subjecting nicotine to a microbiological oxidation as described above to give 5-succinoyl-2-pyridone, subsequently esterifying the 5-succinoyl-2-pyridone to give the alkyl ester (II) or benzyl ester, again as described above, then converting the product into the corresponding chlorine compound by hydroxyl group exchange and subsequently reducing and cyclizing the product to give the lactone of the formula:

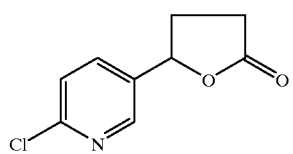

IV

Reduction and cyclization of the ester to the lactone is preferably carried out using a reducing agent from the group of the complex borohydrides. A particularly preferred reducing agent is sodium borohydride. To complete lactone formation, it is advantageous to heat the reaction mixture before or after the reduction.

4-(6-chloropyridine-3-yl)-4-hydroxybutyric acid itself as well as its amide can be prepared according to the invention by first preparing the lactone (IV) as described above and then hydrolyzing the lactone (IV) with a strong aqueous base to give the hydroxy acid or converting with ammonia to give the acid amide. Aqueous strong bases are to be understood as meaning, in particular, alkali metal hydroxide solutions, but not aqueous solutions of primary or secondary amines.

Among the compounds of the first group ($R^2$ and $R^3$ together are =O) where X is chlorine and $R^1$ is OH, the carboxylic acid ($R^4$ is —OH) is prepared according to the invention by converting, in a first step, nicotine into 5-succinoyl-2-pyridone by microbiological transformation as described above and, in a second step, chlorinating the product with chlorine in alkaline solution. The chlorination reaction is preferably carried out in such a way that 5-succinoyl-2-pyridone is converted into the corresponding salt using a strong base, for example, sodium hydroxide, and the solution is brought to a pH of above 10. Chlorine is then passed in, and the pH is maintained above 10 by metering in more base. The reaction temperature is preferably below room temperature, for example, −5° to +10° C. Instead of passing in chlorine gas, the chlorination of reaction can be carried out using a commercially available hypochlorite solution. Working-up can be carried out in a customary manner, excess chlorine or hypochlorite and/or any N-chlorine compounds which have been formed advantageously being decomposed by adding a reducing agent, such as, sodium sulfite.

The corresponding esters (X is Cl, $R^1$ is OH, $R^2$ and $R^3$ together are =O and $R^4$ is —$OR^5$ where $R^5$ is $C_1$–$C_4$ alkyl or benzyl) are prepared according to the invention via the same route, and esterification with a $C_1$–$C_4$-alkanol or benzyl alcohol additionally being carried out as a third step. The esterification can be carried out in a customary manner, for example, with the corresponding $C_1$–$C_4$-alcohol or benzyl alcohol with sulfuric acid as the catalyst.

The compounds of the first group where X and $R^1$ each is Cl and $R^5$ is $C_1$–$C_4$ alkyl or benzyl, are prepared according to the invention by exchanging, in a further step, the hydroxyl group of the esters where $R^1$ is OH which have been obtained as described above for chlorine. This exchange is expediently carried out with an inorganic acid chloride, preferably phosphorus oxychloride.

The corresponding carboxylic acid, i.e., 4-(5,6-dichloropyridine-3-yl)-4-oxobutyric acid, can be obtained from the esters by means of hydrolysis.

The examples which follow illustrate the preparation of the compounds according to the invention and the procedure of the processes according to the invention.

EXAMPLE 1

Isolation of Succinoylpyridone-Forming Microorganisms

Aerobic (S)-nicotine-utilizing microorganisms were enriched in minimal medium (Table 6) with (S)-nicotine as the only carbon source. The general techniques for isolating microorganisms are described, for example, in G. Drews, "Mikrobiologisches Praktikum" [Laboratory Practical in Microbiology], 4th Edition, Springer Verlag, 1983, pages 1–84. Samples from the water treatment plant Visp (Kanton Valais, Switzerland) and a tobacco field in Massongex (Kanton Valais, Switzerland) were used as the inoculum. The enrichment cultures were grown in shake flasks at 30° C. After three transfers to fresh medium, the enrichment cultures were streaked out onto the same medium with an addition of 16 g of agar per liter and incubated at 30° C. After repeated striking onto agar medium, the following pure cultures were isolated:

Pseudomonas putida DSM 8231 (deposited at the DSM on Apr. 26, 1993)
Pseudomonas fluorescens DSM 8235 (deposited at the DSM on Apr. 26, 1993)
Pseudomonas putida DSM 8236 (deposited at the DSM on Apr. 26, 1993)
Variovorax paradoxus (=Alcaligenes paradoxus) DSM 8244 (deposited at the DSM on Apr. 26, 1993)
Pseudomonas sp. DSM 8653 (deposited at the DSM on Oct. 27, 1993)

TABLE 6

Minimal medium

| Composition | Concentration [mg/l] |
|---|---|
| (S)-nicotine | 2000 |
| $(NH_4)_2SO_4$ | 2000 |
| $Na_2HPO_4$ | 2000 |
| $KH_2PO_4$ | 1000 |
| NaCl | 3000 |
| $MgCl_2.6H_2O$ | 400 |
| $CaCl_2.2H_2O$ | 14.5 |
| $FeCl_3.6H_2O$ | 0.8 |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.6H_2O$ | $20 \cdot 10^{-3}$ |
| $NaMoO_4.2H_2O$ | $30 \cdot 10^{-3}$ |
| $EDTANa_2.2H_2O$ | 5 |
| $FeSO_4.7H_2O$ | 2 |

The pH of the solution was brought to 7.0 using $H_3PO_4$.

To determine the metabolic pathway of (S)-nicotine in the microorganisms, samples was taken from a liquid culture during the growth phase. 2 microliters of the cell-free samples was applied to thin-layer plates (Merck, silica gel 60, $F_{254}$) and developed in the following mobile phase: ethanol, 55 ml; chloroform, 30 ml; 25 percent aqueous ammonia, 10 ml; and water, 5 ml. The following $R_f$ values were found: (S)-nicotine, 0.92; 6-hydroxy-(S)-nicotine, 0.70; 4-(pyridine-3-yl)-4-oxobutyric acid, 0.38; and 5-succinoyl-2-pyridone, 0.31. All of the abovementioned Pseudomonas species formed succinoylpyridone via 4-(pyridine-3-yl)-4-oxobutyric acid. Variovorax paradoxus formed succinoylpyridone via 6-hydroxy-(S)-nicotine.

EXAMPLE 2

Biotransformation of (S)-nicotine to 5-succinoyl-2-pyridone Using Pseudomonas sp. DSM 8653

A fermenter of a working volume of 5 liters was inoculated with 400 ml of inoculum of Pseudomonas sp. DSM 8653 in complete medium (Table 7). The fermentation was also carried out using complete medium. The temperature was 30° C. The pH was brought to a value of 7.0 by adding 8.5 percent (v/v) $H_3PO_4$ and 1 M NaOH. Aeration was 1 l/min at the beginning of the fermentation and was increased to 3 l/min after 5 hours. After 7 hours, the optical density of the suspension at 650 nm ($OD_{650}$) was 4.0. At this point in time, 50 g of (S)-nicotine was added to the fermenter, and, simultaneously, a pump was switched on which conveyed 1 liter of feed solution (Table 8) continuously to the fermenter over a period of 15 hours. The nicotine concentration and the concentration of the nicotine metabolites were determined by thin-layer chromatography (see Example 1) and also spectrophotometrically. An ε value of 17000 $M^{-1}$ $cm^{-1}$ was measured for succinoylpyridone at 305 nm in 0.1 M NaOH. At the end of the fermentation after 15 hours, the $OD_{650}$ was 9.2. To isolate the succinoylpyridone formed, the cell-free supernatant was acidified with sulfuric acid until a pH of 25 was reached. Precipitated succinoylpyridone was isolated by filtration and subsequently dried. In total, 70 g of (S)-nicotine was employed in the biotransformation. 77 g of succinoylpyridone was isolated as product, which corresponds to a yield of 91 percent.

TABLE 7

| Complete medium | |
|---|---|
| Composition | Concentration [mg/l] |
| (S)-nicotine | 2000 |
| citric acid | 800 |
| yeast extract | 2000 |
| $(NH_4)_2SO_4$ | 2000 |
| $Na_2HPO_4$ | 2000 |
| $KH_2PO_4$ | 1000 |
| NaCl | 3000 |
| $MgCl_2.6H_2O$ | 400 |
| $CaCl_2.2H_2O$ | 14.5 |
| $FeCl_3.6H_2O$ | 0.8 |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.6H_2O$ | $20 \cdot 10^{-3}$ |
| $NaMoO_4.2H_2O$ | $30 \cdot 10^{-3}$ |
| $EDTANa_2.2H_2O$ | 5 |
| $FeSO_4.7H_2O$ | 2 |

The pH of the solution was brought to a value of 7.0 using $H_3PO_4$.

TABLE 8

| Feed solution | |
|---|---|
| Composition | Concentration [mg/l] |
| (S)-nicotine | 20000 |
| citric acid | 8000 |
| yeast extract | 20000 |

EXAMPLES 3 TO 5
Biotransformation of (S)-nicotine to 5-succinoyl-2-pyridone
Examples 3 to 5 were carried out analogously to Example 2. The results are shown in Table 9:

TABLE 9

| Ex. | Strain | Amount of succinoyl pyridone isolated | Yield |
|---|---|---|---|
| 3 | P. putida DSM 8231 | 45 g | 53% |
| 4 | P. fluorescens DSM 8235 | 40 g | 47% |
| 5 | V. paradoxus DSM 8244 | 62 g | 73% |

EXAMPLE 6
4-(5-Chloro-1,6-dihydro-6-oxopyridin-3-yl)-4-oxobutyric acid 25 g (128 mmol) of 5-succinoyl-2-pyridone was suspended in 250 ml of water at room temperature. The pH was brought to 10.5 by adding 30 percent sodium hydroxide solution, resulting in a clear solution. The solution was cooled to 2° C. Chlorine gas was slowly passed in, the pH being kept at between 10.2 and 105 by metering in sodium hydroxide solution and the temperature being kept below 6° C by means of cooling. In total, 13.2 g of chlorine and 72.4 g of 30 percent sodium hydroxide solution were consumed. To destroy excess chlorine or N-chlorinated compounds, 19.2 g (152 mmol) of sodium sulfite was added, and the mixture was heated to 40° C. The mixture was then acidified to a pH of 2 using concentrated hydrochloric acid, during which process the desired product precipitated. The suspension was stirred at room temperature for another 2 hours, cooled to 2° C. and filtered. The product yield was 19.66 g (67%) of white solid. Other data concerning the product was:

$^1$H NMR (DMSO-$d_6$): δ 2.52 (t, J=6.8 Hz, 2H); 3.08 (t, J=6.8 Hz, 2H); 8.07 (d, J=3.5 Hz, 1H); 8.30 (d, J=3.5 Hz, 1H); 12.18 (br.s,1H); 12.77 (br.s,1H).

EXAMPLE 7
Methyl 4-(5-Chloro-1,6-dihydro-6-oxopyridin-3-yl)-4-oxobutyrate 43 g of 4-(5-chloro-1,6-dihydro-6-oxopyridin-3-yl)-4-oxobutyric acid (crude product, prepared as described in Example 6) was suspended in 730 ml of methanol, and 16 ml of concentrated sulfuric acid was added. The mixture was heated in such a way that approximately 100 ml of methanol distilled off in the course of 4 hours. The reaction mixture which remained was then concentrated to half its volume under reduced pressure and the resulting solution was cooled to 2° C. The product was removed by filtration, washed using 20 ml of cold methanol and dried. The product yield was 38.1 g (83%) of white crystals. The product melting point was 211.5° to 213.5° C. Other data concerning the product was:

$^1$H NMR (DMSO-$_6$): δ 2.60 (t, J=7.8 Hz,2H); 3.15 (t, J=7.8 Hz,2H); 359 (s, 3H); 8.07 (d, J=3.5 Hz,1H); 832 (d, J=35 Hz,1H); 12.78 (br.s,1H).

EXAMPLE 8
Methyl 4-(5-chloro-1,6-dihydro-6-oxopyridin-3-yl)-4-oxobutyrate

This compound was also obtained in 28 percent yield by chlorinating 5-succinoyl-2-pyridone methyl ester (obtained analogously to Example 7 from 5-succinoyl-2-pyridone and methanol/sulfuric acid) using chlorine in methanol. The main product obtained (70 percent yield) was methyl 4-(3,5-dichloro-2-methoxy-6-oxo-1,2,3,6-tetrahydropyridin-3-yl)-4-oxobutyrate, which was characterized by the following data:

$^1$H NMR (CDCL): δ 2.69 (t, J=6.9 Hz,2H) 2.83 (m, 1H) 3.28 (m, 1H) 3.42 (s, 3H) 3.72 (s, 3H); 5.01 (dd, J=4.6 Hz,1.8 Hz,1H); 7.22 (d, J=1.8 Hz,1H); 8.57 (d, J=4.6 Hz,1H).

$^{13}$C NMR (CDCl$_3$): δ 28.02, 31.05, 52.02, 55.86, 64.75, 86.59 130.29, 133.50, 160.00, 172.55, 196.27.

Calc. C 42.6 H 4.2 N 4.5 Found C 42.9 H 4.3 N 4.5

EXAMPLE 9
Methyl 4-(5,6-dichloropyridin-3-yl)-4-oxobutyrate

A suspension of 37 g (152 mmol) of methyl 4-(5-chloro-1,6-dihydro-6-oxopyridin-3-yl)-4-oxobutyrate in 230 ml of phosphorus oxychloride was heated at 75° C. for 25 hours. The phosphorus oxychloride was subsequently distilled off in vacuo. The pale red residue was taken up in 200 ml of dichloromethane, 100 ml of water was added, and the pH of the aqueous phase was brought to 8.5 using 30 percent sodium hydroxide solution. After phase separation, the aqueous phase was extracted using 100 ml of dichloromethane. The combined organic phases were treated with active charcoal and evaporated. The residue was recrystallized from 300 ml of diisopropyl ether and filtered at 2° C. The yield was 32.83 g of pale pink crystals. A further 1.76 g of product was obtained from the mother liquor in the form of crystals. The total product yield was 87 percent. The melting point of the product was 85.2° to 86° C. Other data concerning the product was:

$^1$H NMR (CDCl$_3$): δ 2.83 (t, J=7.8 Hz,2H); 3.29 (t, J=7.8 Hz,2H); 3.73 (s,3H); 8.33 (d, J=2.4 Hz,1H); 8.87 (d, J=2.4 Hz, 1H).

EXAMPLE 10
5-Succinoyl-2-pyridone methyl ester
Methyl 4-(1,6-dihydro-6-oxopyridin-3-yl)-4-oxobutyrate A suspension of 27 g (138 mmol) of 5-succinoyl-2-pyridone in 400 ml of methanol was treated with 10.4 g of concentrated sulfuric acid and the mixture was heated at 63° C. for 2 hours, during which process 100 ml of methanol distilled off. After cooling to room temperature, the resultant brown solution was placed in a refrigerator, where the product crystallized out. The ester was filtered off, washed using cold methanol and dried in vacuo. The product yield was 23.5 g (81%) of white crystals. The melting point of the product was 167° to 168° C. Other data concerning the product was:

$^1$H NMR (DMSO-d$_6$): δ 2.59 (t, J 7.5 Hz,2H); 3.13 (t, J=7.5 Hz,2H); 3.58 (s,3H); 6.37 (d, J=12 Hz, 1H); 7.86 (dd, J=12 Hz, 3.5 Hz,1H); 8.27 (d, J=3.5 Hz,1H); 12.14 (br.s,1H).

MS (EI) m/z (%): 209 [M$^+$], 178, 150, 122 (100%)

EXAMPLE 11
5-Succinoyl-2-pyridone ethyl ester
Ethyl 4-(1,6-dihydro-6-oxopyridin-3-yl)-4-oxobutyrate The ester was prepared analogously to the methyl ester (Example 10) using ethanol/sulfuric acid. The melting point of the product was 121.8° to 122.7° C. Other data concerning the product was:

$^1$H NMR (DMSO-d$_6$): δ 1.18 (t, J=8.2 Hz,1H); 2.58 (t, J=7.5 Hz,2H); 3.11 (t, J=7.5 Hz,2H); 4.05 (q, J=8.2 Hz,2H); 6.37 (d, J=12 Hz,2H); 7.86 (dd, J=12 Hz,3.5 Hz,1H); 8.26 (d, J=3.5 Hz,1H); 12.18 (br.s,1H).

EXAMPLE 12
2-Chloro-5-succinoylpyridine methyl ester
Methyl 4-(6-chloropyridin-3-yl)-4-oxobutyrate 25 g (119 mmol) of 5-succinoyl-2-pyridone methyl ester (prepared as described in Example 10) was suspended in 110 ml of phosphorus oxychloride at 20° C. The mixture was carefully heated at 70° C. and held at this temperature for 1 hour. The phosphorus oxychloride was distilled off under reduced pressure. The brown oily residue, in each case, was taken up in 100 ml of toluene and water, and the aqueous phase was brought to pH 9 using 30 percent sodium hydroxide solution and extracted twice using toluene. The combined toluene extracts were evaporated. The residue, a pale red oil (26.15 g), was treated with active charcoal and then crystallized from diisopropyl ether. The product yield was 24.14 g (89%) of white crystals. The melting point of the product was 73.4° to 74° C. Other data concerning the product was:

$^1$H NMR (CDCl$_3$): δ 2.81 (t, J=7.5 Hz,2H); 3.32 (t, J=7.5 Hz,2H); 3.72 (s,3H); 7.47 (d, J=10.2 Hz,1H); 8.23 (dd, J=10.2 Hz,3.6 Hz, 1H); 8.97 (d, J=3.6 Hz, 1H).

EXAMPLE 13
6-(1,6-Dihydro-6-oxopyridin-3-yl)-2,3,4,5-tetrahydropyridazin-3-one 5 g (23.9 mmol) of succinoyl-2-pyridone methyl ester (prepared as described in Example 10) was suspended in 67 ml of ethanol and the suspension was treated with 2.4 g (48 mmol) of hydrazine hydrate. The mixture was heated at 70° C., during which process the educt dissolved. The colorless solution was refluxed overnight, during which process a dense white precipitate formed. After cooling, this precipitate was filtered off, washed using ethanol and dried in vacuo. The product yield was 4.33 g (95%). The melting point of the product was >260° C. Other data concerning the product was:

$^1$H NMR (DMSO-d$_6$): δ 2.38 (t, J=9.6 Hz,2H); 2.80 (t, J=9.6 Hz,2H); 6.38 (d, J=12 Hz,1H); 7.69 (d, J=3 Hz,1H); 7.90 (dd, J=12 Hz,3 Hz,1H); 10.80 (s,1H), 11.84 (br.s,1H).

Calc. C 56.54 H 4.75 N 21.98 Found C 56.44 H 4.75 N 21.61

EXAMPLE 14
6-(6-Chloropyridin-3-yl)-2,3,4,5-tetrahydropyridazin-3-one 1.13 g (22.6 mmol) of hydrazine hydrate was added at room temperature to a solution of 3 g (13.2 mmol) of 2-chloro-5-succinoylpyridine methyl ester (prepared as described in Example 12) in 55 ml of a mixture of toluene and methanol (7:4). The mixture was stirred for 5 hours, during which process the product precipitated gradually. The suspension was cooled to 2° C. and filtered. The precipitate was washed using a small amount of cold toluene/methanol mixture and dried. The product yield was 1.86 g (67%) of white needles. Evaporation of the mother liquor gave 1 g of a residue which was essentially also composed of the desired product. The melting point of the product was 210.8° to 211.8° C. Other data concerning the product was:

$^1$H NMR (DMSO-d$_6$): δ 2.50 (t, J=9.6 Hz,2H); 2.98 (t, J 9.6 Hz,2H); 7.58 (d, J=10.2 Hz,1H); 8.17 (dd, J=10.2 Hz, 3.6 Hz,1H); 8.74 (d, J=3.6 Hz,1H); 11.11 (s,1H).

EXAMPLE 15
5-(5-Chloropyridin-3-yl)-tetrahydrofuran-2-one 1.97 g (52 mmol) of sodium borohydride was added, a little at a time, to a solution of 15 g (66 mmol) of methyl 4-(6-chloropyridin-3-yl)-4-oxobutyrate (prepared as described in Example 12) in 220 ml of methanol at 25° C. in the course of 20 minutes. The reaction mixture was stirred for 1 hour and treated with 200 ml of toluene, and the methanol was distilled off. The mixture was then heated at 100° C. for a further hour to complete lactone formation. The mixture was subsequently filtered and the filtrate evaporated. The residue (13.3 g of pale brown oil) was crystallized from 70 ml of diisopropyl ether. The product yield was 11.95 g (92%) of white solid. The melting point of the product was 52.5° to 53° C. Other data concerning the product was:

$^1$H NMR (CDCl$_3$): δ 2.20 (m,1H); 2.72 (m,2H); 2.76 (m,1H); 5.54 (m,1H); 7.49 (d, J=10.2 Hz, 1H); 7.68 (d, J=10.2 Hz, 3 Hz, 1H); 8.38 (d, J=3 Hz, 2H).

$^{13}$C NMR (CDCl$_3$): δ 28.77, 30.63, 78.19, 124.55, 134.12, 136.10, 147.13, 151.69, 176.02.

EXAMPLE 16
4-(6-Chloropyridin-3-yl) 4hydroxybutyramide 3.6 g of 5-(6-chloropyridin-3-yl)tetrahydrofuran-2-one (prepared as described in Example 15) was dissolved in 30 ml of 25 percent aqueous ammonia solution and the mixture was heated at 45° C. for 1.5 hours. The solution was evaporated in vacuo. The oily residue (4.65 g) was dried in vacuo over phosphorus pentoxide. The product yield was 3.9 g (approximately 100%) of rubber-like product. Other data concerning the product was:

$^1$H NMR (DMSO-d$_6$): δ 1.85 (m, 2H); 2.12 (t, J=7.5 Hz,2H); 4.63 (m, 1H); 5.57 (d, J=6 Hz, 1H); 6.76 (br.s.1H); 7.30 (br.s.1H); 7.48 (d, J=9.6 Hz, 1H); 7.80 (dd, J=9.6 Hz, 3.5 Hz, 1H); 8.35 (d, J=3.5 Hz, 1H).

EXAMPLE 17

4-(6-Chloropyridin-3-yl)-4-hydroxybutyric acid

The acid was obtained in virtually quantitative yield by reacting 5-(6-chloropyridin-3-yl)tetrahydrofuran-2-one (prepared as described in Example 15) with aqueous sodium hydroxide at pH 13 and room temperature. After neutralization with hydrochloric acid, the reaction mixture was evaporated and the residue recrystallized from ethanol. In this way, the acid was obtained in the form of white crystals. Data concerning the product was:

$^1$NMR (CDCl$_3$): δ 2.06 (m, 2H); 2.54 (m, 2H); 4.85 (t, 1H); 7.33 (d, 1H); 7.73 (dd, 1H); 8.38 (d, 1H).

$^{13}$C NMR (DMSO$_6$): δ 34.97, 35.35, 70.38, 123.5, 137.23, 141.63, 147.60, 148.14, 178.19.

MS of the bistrimethyl- 359/361 (M$^+$), 214/216 (100%) silyl compound: m/z The intensities correspond to the isotope ratio of chlorine.

What is claimed is:

1. A Pyridyl-Pyridazinone derivative of the formula:

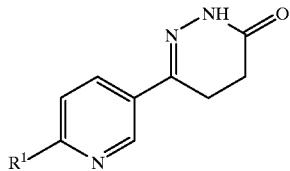

III wherein R$^1$ represents hydroxy or chlorine.

* * * * *